United States Patent [19]
Al-Razzak et al.

[11] Patent Number: 6,010,718
[45] Date of Patent: Jan. 4, 2000

[54] EXTENDED RELEASE FORMULATIONS OF ERYTHROMYCIN DERIVATIVES

[75] Inventors: Laman Al-Razzak, Highland Park; Sheri L. Crampton, Gurnee; Linda E. Gustavson, Evanston; Ho-Wah Hui, Libertyville; Nelly Milman, Skokie; Susan J. Semla, Evanston, all of Ill.

[73] Assignee: Abbott Laboratories, Abbott Park, Ill.

[21] Appl. No.: 08/838,900

[22] Filed: Apr. 11, 1997

[51] Int. Cl.[7] .............................. A61K 9/20; A61K 9/22; A61K 9/36

[52] U.S. Cl. ......................... 424/464; 424/468; 424/480

[58] Field of Search .................................. 424/439, 441, 424/480, 494, 484, 401, 462, 468, 486, 488; 514/927

[56] References Cited

U.S. PATENT DOCUMENTS

| | | | |
|---|---|---|---|
| 3,870,790 | 3/1975 | Lowey et al. | 424/19 |
| 4,226,849 | 10/1980 | Schor | 424/19 |
| 4,369,172 | 1/1983 | Schor et al. | 424/19 |
| 4,808,411 | 2/1989 | Lu et al. | 424/441 |
| 4,842,866 | 6/1989 | Horder et al. | 424/468 |
| 5,393,765 | 2/1995 | Infeld et al. | 514/365 |

FOREIGN PATENT DOCUMENTS

| | | |
|---|---|---|
| 0293885 | 12/1988 | European Pat. Off. . |
| 2585948 | 2/1987 | France . |
| 9530422 | 11/1995 | WIPO . |
| 9722335 | 6/1997 | WIPO . |

OTHER PUBLICATIONS

Die Pharmazie, vol. 50, No. 4 (Feb. 1995), pp. 154–155, J. Rak et al., "Matrixtabletten aus Niedrigviskoser Hydropromellose".

Journal of Controlled Release, vol. 12 (1990), pp. 133–141, K.V. Ranga Rao et al., "Influence of Molecular Size and Water Solubility of the Solute on Its Release from Swelling and Erosion Controlled Polymeric Matrices".

*Primary Examiner*—Thurman K. Page
*Assistant Examiner*—Sharon Howard
*Attorney, Agent, or Firm*—Mona Anand

[57] ABSTRACT

Disclosed is a pharmaceutical composition for extended release of an erythromycin derivative in the gastrointestinal environment. The composition comprises an erythromycin derivative and a pharmaceutically acceptable polymer so that, when ingested orally, the composition induces statistically significantly lower $C_{max}$ in the plasma than an immediate release composition of the erythromycin derivative while maintaining bioavailability and minimum concentration substantially equivalent to that of the immediate release composition of the erythromycin derivative upon multiple dosing. The compositions of the invention have an improved taste profile and reduced gastrointestinal side effects as compared to those for the immediate release composition.

16 Claims, 3 Drawing Sheets

EXTENDED RELEASE FORMULATIONS OF ERYTHROMYCIN DERIVATIVES

TECHNICAL FIELD

The present invention relates to pharmaceutical compositions of erythromycin derivatives with an extended release of an active compound in the gastrointestinal environment. More particularly, it relates to pharmaceutical compositions of clarithromycin which are ingested daily as a single oral administration.

BACKGROUND OF THE INVENTION

Erythromycin and its derivatives are known for their antibacterial activity against a number of organisms or activity in a number of indications and are typically administered as immediate release (IR) compositions, two or three times a day, for a regimen of 10 to 14 days. These compounds have a bitter taste. In particular, the 6-O-methoxyerythromycin A (clarithromycin) has a bitter metallic taste which can result in poor compliance of the regimen or selection of another, possibly less effective, therapeutic agent.

One approach to improve the possible non-compliance with the regimen has been to develop controlled release solid preparations containing these erythromycin derivatives in an alginate matrix comprising a water-soluble alginate and a complex salt of alginic acid, having one cation that yields a soluble alginate salt and another cation that alone yields an insoluble alginate salt. These formulations are described in U.S. Pat. No. 4,842,866, issued Jun. 27, 1989. However, in-vivo animal studies showed that reproducibly bioavailable controlled release formulation were not possible using alginates or any other monolithic hydrogel tablets.

To overcome some of the problems associated with the formulations described in U.S. Pat. No. 4,842,866, improved controlled release formulations for poorly soluble basic drugs such as erythromycin derivatives including clarithromycin, have been developed and are described in commonly owned, co-pending U.S. patent application Ser. No. 08/574,877, filed Dec. 19, 1995. The formulations described in the patent application comprise a poorly soluble basic drug and citric acid in an alginate matrix. The formulations are administered once a day and are directed towards increasing the bioavailability of the active ingredient so that it is bioequivalent with the current immediate release, twice-a-day compositions. However, these controlled release compositions do not purport to minimize the adverse effects related to gastrointestinal (GI) disorders including nausea and vomiting and a phenomenon described as taste perversion.

One approach to address taste perversion has been to develop acceptable palatable liquid oral dosage forms of these drugs as described in U.S. Pat. No. 4,808,411, issued Feb. 28, 1989. However, these formulations are administered twice-a-day for a period of 10 to 14 days and do not address the frequency and duration of the administration regimen, or the adverse effects related to GI disorders. Therefore, there still exists a need for developing a pharmaceutical composition which minimizes the adverse effects described above and provides a degree of drug plasma concentration control which is equivalent to or better than the (IR) tablet or liquid formulations currently used.

SUMMARY OF THE INVENTION

It has been discovered that the extended release (ER) formulations of the present invention which comprise a pharmaceutically acceptable polymer, provide extended release clarithromycin in vivo when given once daily. Maximum concentrations ($C_{max}$) of clarithromycin in plasma are statistically significantly lower than the IR formulation given twice daily, and area under the plasma concentration-time curve (AUC) and the minimum plasma concentration are maintained over 24 hours. In contrast, for the controlled release formulations described in the co-pending U.S. application Ser. No. 08/574,877, filed Dec. 19, 1995, the $C_{max}$ values are not statistically significantly different from those for the IR formulation. And while the $AUC_{0-24}$ is maintained, the $C_{min}$ is statistically significantly lower for the controlled-release formulations relative to the IR formulation. The compositions of the invention have surprisingly a two-to three-fold reduction in incidence rates for taste perversion compared to the IR formulation.

In one aspect, the present invention relates to a pharmaceutical composition for extended release of an erythromycin derivative in the gastrointestinal environment, comprising an erythromycin derivative and a pharmaceutically acceptable polymer, so that when ingested orally, the composition induces statistically significantly lower mean fluctuation index in the plasma than an immediate release composition of the erythromycin derivative while maintaining bioavailability substantially equivalent to that of the immediate release composition of the erythromycin derivative.

In another aspect, the present invention relates to a pharmaceutical composition for extended release of an erythromycin derivative in the gastrointestinal environment, comprising an erythromycin derivative and a pharmaceutically acceptable polymer, so that upon oral ingestion, maximum peak concentrations of the erythromycin derivative are statistically significantly lower than those produced by an immediate release pharmaceutical composition, and an area under the concentration-time curve and the minimum plasma concentration are substantially equivalent to that of the immediate release pharmaceutical composition.

In yet still another aspect, the present invention relates to a method of using an extended release, pharmaceutical composition comprising an erythromycin derivative and a pharmaceutically acceptable polymer, comprising administering the composition in an effective amount for the treatment of bacterial infection in a mammal, whereby an area under the concentration-time curve equivalent to that for an immediate release pharmaceutical composition of the erythromycin derivative is maintained.

In yet another aspect, the present invention is an extended release pharmaceutical composition comprising an erythromycin derivative and a pharmaceutically acceptable polymer, wherein the composition has an improved taste profile relative to the immediate release formulation.

DETAILED DESCRIPTION OF THE INVENTION

Figure 1:
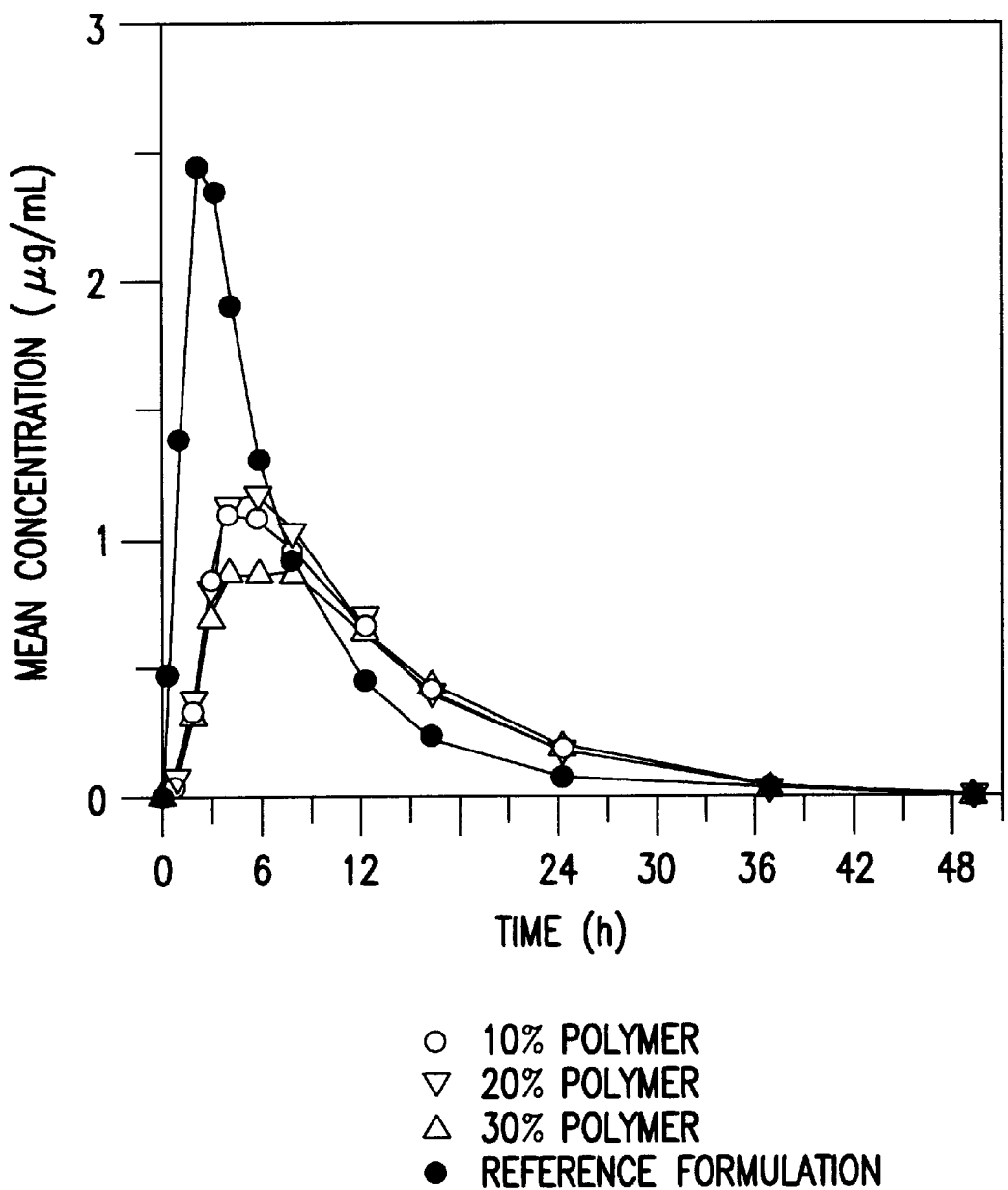
FIG. 1 illustrates the mean in vivo plasma concentration-time profiles following single dose of three 500 mg ER tablets containing clarithromycin and 10%, 20% or 30%, respectively, by weight of hydroxy-propylmethyl cellulose K 100 LV, as compared to that of the reference 500 mg IR clarithromycin tablet.

"500 mg or 1000 mg" as used herein, means the strength of tablet composition containing 500 mg clarithromycin, or the dose administered as 2×500 mg of clarithromycin, respectively.

"$C_{max}$" as used herein, means maximum plasma concentration of the erythromycin derivative, produced by the ingestion of the composition of the invention or the IR comparator.

"$C_{min}$" as used herein, means minimum plasma concentration of the erythromycin derivative, produced by the ingestion of the composition of the invention or the IR comparator.

"$C_{avg}$" as used herein, means the average concentration within the 24-hour interval.

"$T_{max}$" as used herein, means time to the maximum observed plasma concentration.

"AUC" as used herein, means area under the plasma concentration-time curve, as calculated by the trapezoidal rule over the complete 24-hour interval for all the formulations.

"Degree of Fluctuation (DFL)" as used herein, is expressed as:

$$DFL=(C_{max}-C_{min})/C_{avg}.$$

"Erythromycin derivative" as used herein, means erythromycin having no substituent groups, or having conventional substituent groups, in organic synthesis, in place of a hydrogen atom of the hydroxy groups and/or a methyl group of the 3'-dimethylamino group, which is prepared according to the conventional manner.

"Pharmaceutically acceptable" as used herein, means those compounds which are, within the scope of sound medical judgment, suitable for use in contact with the tissues of humans and lower animals without undue toxicity, irritation, allergic response, and the like, in keeping with a reasonable benefit/risk ratio, and effective for their intended use in the chemotherapy and prophylaxis of antimicrobial infections.

"Adverse effects" as used herein, means those physiological effects to various systems in the body such as cardiovascular systems, nervous system, digestive system, and body as a whole, which cause pain and discomfort to the individual subject.

"Taste perversion" as used herein, means the perception of a bitter metallic taste normally associated with the erythromycin derivatives, particularly, with clarithromycin.

The pharmaceutical composition of the invention comprise a pharmaceutically active compound and a pharmaceutically acceptable polymer. The pharmaceutically active compound is an erythromycin derivative. Preferably, the erythromycin derivative is 6-O-methoxy erythromycin A, known as clarithromycin. The amount of the erythromycin derivative varies from about 45% to about 60% by weight of the composition. Preferably, the composition comprises about 50% by weight of the erythromycin derivative.

The pharmaceutically acceptable polymer is a water-soluble hydrophilic polymer selected from the group consisting of polyvinylpyrrolidine, hydroxypropyl cellulose, hydroxypropylmethyl cellulose, methyl cellulose, vinyl acetate/crotonic acid copolymers, methacrylic acid copolymers, maleic anhydride/methyl vinyl ether copolymers and derivatives and mixtures thereof. Preferably, the polymer is selected from hydroxypropyl cellulose, hydroxypropylmethyl cellulose, and methyl cellulose. More preferably, the polymer is hydroxypropylmethyl cellulose. Most preferably, the polymer is a low viscosity hydroxypropyl-methyl cellulose with viscosity ranging from about 50 cps to about 200 cps. The most preferred low viscosity polymer is a hydroxypropylmethyl cellulose with a viscosity of about 100 cps, commercially available under the Tradename Methocel™ K 100 LV from The Dow Chemical Company.

The amount of the polymer in the composition generally varies from about 5% to about 50% by weight of the composition. Preferably, the amount of polymers varies from about 10% to about 35% by weight of the composition. Most preferably, the amount of polymer varies from about 10% to about 30% by weight of the polymer.

The composition of the invention further comprise pharmaceutically acceptable excipients and/or fillers and extenders, such as lactose, starches, glucose, sucrose, mannitol, and silicic acid, lubricants such as talc, calcium stearate, magnesium stearate, solid polyethylene glycols, sodium lauryl sulfate, and mixtures thereof.

The amount of the lubricants generally varies from about 0.5% to about 10% by weight of the composition. Preferably, the lubricants used are magnesium stearate and talc in the total amounts ranging from about 1.0% to about 4.0% by weight of the composition. The amount of fillers and extenders varies from about 10% to about 40% by weight of the composition.

A particularly preferred composition for the extended release of the active compound therefrom comprises:
about 500 mg of clarithromycin; and
from 100 to 300 mg of Methocel K 100 LV.

The formulations are generally prepared by dry blending the polymer, filler, erythromycin derivative, and other excipients followed by granulating the mixture using water until proper granulation is obtained. The granulation is done by methods known in the art. The wet granules are dried in a fluid bed dryer, sifted and ground to appropriate size. Lubricating agents are mixed with the dried granulation to obtain the final formulation.

The compositions of the invention can be administered orally in the form of tablets, pills, or suspensions. The tablets can be prepared by techniques known in the art and contain a therapeutically useful amount of erythromycin derivative and such excipients as are necessary to form the tablet by such techniques. Tablets and pills can additionally be prepared with enteric coatings and other release-controlling coatings for the purpose of light protection, and swallowability. The coating may be colored with a pharmaceutically accepted dye. The amount of dye and other excipients in the coating liquid may vary and will not impact the performance of the extended release tablets. The coating liquid generally comprises film forming polymers such as hydroxy-propyl cellulose, hydroxypropylmethyl cellulose, cellulose ester or ether, an acrylic polymer or a mixture of polymers. The coating solution is generally an aqueous solution further comprising propylene glycol, sorbitan monoleate, sorbic acid, fillers such as titanium dioxide, a pharmaceutically acceptable dye.

Liquid dosage forms for oral administration may include pharmaceutically acceptable emulsions, microemulsions, solutions, suspensions, syrups and elixirs containing inert diluents commonly used in the art such as water. Such compositions may also comprise adjuvants, such as wetting agents; emulsifying and suspending agents; and sweetening, flavoring and perfuming agents.

The daily dose of the composition of this invention administered to a host in single dose can be in the amounts from 500 mg to 1000 mg once-a-day for five to fourteen days.

Pharmacokinetic Study

The bioavailability study for the formulations of the invention can be done by administering the ER formulation in a tablet form to healthy subjects and measuring the levels of erythromycin derivative in the plasma at different time intervals over a period of twenty four hours.

Plasma samples are assayed for erythromycin derivative at BAS Analytics (West Lafayette, Ind.) using a validated high-performance liquid chromatographic procedure similar to that described in the literature. See for example, Chu S-Y, et al., "Simultaneous determination of clarithromycin and 14(R)-hydroxyclarithromycin in plasma and urine using high-performance liquid chromatography with electrochemical detection", *J. Chromatog.*, 571, pp 199–208 (1991).

Adverse Effects and Taste Profile

Adverse effects including those related to the digestive system, nervous system, respiratory system and special senses, including taste perversion, are measured by dosing subjects with multiple doses of 1000 mg of ER and IR tablets per day, respectively. The adverse effects are monitored, reported spontaneously by subjects and recorded on case report forms for the study database.

The invention will be understood more clearly from the following Examples, which are given solely by way of illustration and serve to provide a clear understanding of the invention and to illustrate its different embodiments as well as its various advantages.

EXAMPLES

Example 1

Preparation of Formulation

Methocel™ (K 100 LV) available from The Dow Chemical Company was loaded into a mixer, and dry blended with clarithromycin. The mixture was granulated using water until proper granulation was obtained. The granulation was then dried, sifted and ground to appropriate size.

Talc and magnesium stearate were screened and blended with dry granulation. The granulation was then loaded into hopper and compressed into tablets. The tablets were then coated with an aqueous coating.

Three different formulations A, B, and C were prepared according to the general method described above. The compositions of three different tablet formulations are given below in Table 1.

TABLE 1

| Ingredient | A mg/tablet | B mg/tablet | C mg/tablet |
| --- | --- | --- | --- |
| Water (USP, purified) | Q.S. | Q.S. | Q.S. |
| Clarithromycin | 500.00 | 500.00 | 500.00 |
| Methocel K 100 LV Premium CR Grade* | 200.00 | 100.00 | 300.00 |
| Lactose, monohydrate | 260.00 | 360.00 | 160.00 |

TABLE 1-continued

| Ingredient | A mg/tablet | B mg/tablet | C mg/tablet |
| --- | --- | --- | --- |
| Talc, USP | 30.00 | 30.00 | 30.00 |
| Magnesium Stearate | 10.00 | 10.00 | 10.00 |

*Available from The Dow Chemical Company

Example 2

Pharmacokinetic Study of the Extended Release Formulation

The bioavailability study to determine the concentration-time plasma profile was done on healthy subjects. The study was conducted as a Phase I, single-dose, open, randomized, four-period, balanced cross-over study described below.

Single-Dose Study

Twenty-four (24) healthy adult subjects were enrolled and 23 completed all phases of the study. For the 23 subjects who completed all phases of the study (12 males, 11 females), the mean age was 29 years (range: 19 to 49 years), the mean weight was 69.0 kg (range: 51.5 to 85 kg) and the mean height was 172 cm (range: 157 to 192 cm).

Clarithromycin 500 mg extended release tablets corresponding to the formulations A, B, and C of Example 1 and the 500 mg IR clarithromycin tablet (Reference Formulation), currently sold by Abbott Laboratories under the Tradename BIAXIN™, were administered to the 23 healthy subjects.

The study was conducted according to a single-dose, open-label, randomized four-period crossover design in which each subject received a single 500 mg dose of clarithromycin during each 30 minutes period after starting breakfast. Wash-out periods of one week separated the doses.

Seven (7) ml blood samples were collected prior to dosing (0 hour) and at 0.5, 1.0, 2.0, 3.0, 4.0, 6.0, 8.0, 12.0, 16.0, 24.0, 36.0 and 48.0 hour after each dose. Plasma samples were assayed for clarithromycin at BAS Analytics (West Lafayette, Ind.) using a validated high performance liquid chromatographic procedure.

Pharmacokinetic Analyses

Values for clarithromycin pharmacokinetic parameters, including observed $C_{max}$, $T_{max}$, and $AUC_{0-\infty}$, were calculated using standard noncompartmental methods.

The mean plasma concentration-time profiles for the single-dose study are illustrated in FIG. 1.

FIG. 1 illustrates that all the three formulations of the invention are substantially equivalent in extended release of clarithromycin over a period of 24 hours.

Table II summarizes the pharmacokinetic results obtained after single-dosing in the above study.

TABLE II

| Formulation | $C_{max}$ (µg/ml) | $T_{max}$ (h) | $AUC_{0-\infty}$ (µg·h/mL) |
| --- | --- | --- | --- |
| A | 1.19 ± 0.60* | 5.0 ± 1.7* | 15.0 ± 6.5* |
| B | 1.33 ± 0.70*# | 5.5 ± 2.4* | 15.1 ± 6.5* |
| C | 1.01 ± 0.48* | 5.5 ± 2.2* | 14.8 ± 7.5* |
| Reference Tablet | 2.57 ± 0.70 | 2.2 ± 0.5 | 17.7 ± 5.6 |

*Statistically significantly different from the IR reference tablet
Statistically significantly different from Formulations A and C in analysis of logarithms Statistical Analyses For $C_{max}$, $AUC_{0-\infty}$, $T_{max}$, and the logarithms of $C_{max}$, and $AUC_{0-\infty}$, an analysis of variance (ANOVA) was performed with sequence, subject nested within sequence, period and formulation as the sources of variation. Effects for subjects were random and all other effects were fixed. Within the framework of ANOVA, the formulations were compared pairwise, with each test at a significance level of 0.05. Also within the framework of the ANOVA for the logarithm of $AUC_{0-\infty}$, bioequivalence of the ER formulations to the IR reference formulation was assessed using the two one-sided tests procedure via 90% confidence intervals. The confidence intervals were obtained by exponetiating the endpoints of the confidence intervals for the difference of logarithm means.

Point estimates of relative bioavailability and 90% confidence intervals for the two one-sided tests procedure from analysis of log-transformed $AUC_{0-\infty}$ are set forth in Table III below.

TABLE III

| Formulation Comparison | Relative Bioavailability | |
|---|---|---|
| | Point Estimate | 90% Confidence Interval |
| A vs Reference | 0.815 | 0.737–0.902 |
| B vs Reference | 0.835 | 0.755–0.925 |
| C vs Reference | 0.787 | 0.711–0.871 |

The $AUC_{0-\infty}$ central values were lower for the three ER formulations than for the reference IR tablet. The lower $C_{max}$ values and the later $T_{max}$ values suggest that all the ER formulations with varying weight percent of polymer, provide extended-release of clarithromycin in vivo.

The lower $AUC_{0-\infty}$ values for the ER formulations may suggest that for a single 500 mg dose administered under nonfasting conditions, the extent of absorption of clarithromycin was reduced relative to that of the reference IR tablet.

Multiple-Dose Study

Twenty-four (24) healthy adult subjects were enrolled and 23 completed all phases of the study. Of the 23 who completed the study (19 males, 4 females), the mean age was 30 years (range: 20 to 47 years), the mean weight was 72 kg (range: 51 to 87 kg) and the mean height was 176 cm (range: 159 to 189.5 cm).

The clarithromycin dosage forms included 500 mg ER tablets of Example 1 containing 10% or 20% by weight of K 100 LV, respectively, and a reference 500 mg IR tablet (BIAXIN).

The study was conducted according to a single- and multiple-dose, open-label, randomized three-period cross-over design.

Regimen A

A single 1000 mg dose of ER formulation A tablets (two 500 mg tablets) was administered in the morning on Day 1. Beginning on Day 3, a multiple dose regimen of 1000 mg clarithromycin (two 500 mg tablets) was administered each morning for three days (Days 3–5).

Regimen B

A single 1000 mg dose of ER formulation B tablets (two 500 mg tablets) was administered in the morning on Day 1. Beginning on Day 3, a multiple dose regimen of 1000 mg clarithromycin (two 500 mg tablets) was administered each morning for three days (Days 3–5).

Regimen C

A single 500 mg dose of IR tablet (BIAXIN) was administered in the morning on Day 1. Beginning on Day 3, a multiple dose regimen of 500 mg reference tablet BIAXIN was administered every twelve hours for three days.

Each morning dose was administered thirty minutes after breakfast. Every evening dose was administered thirty minutes after starting the evening snack.

Wash-out periods of at least one week separated the last dose in a period and the first dose in the following period.

Seven (7) ml blood samples were collected before dosing on Day 1 (0 hr) and at 0.5, 1.0, 2.0, 3.0, 4.0, 6.0, 8.0, 12.0, 16.0, 24.0, 36.0, and 48.0 hour after dosing. For Regimen C, the 12 hour sample was collected within 5 minutes before the evening dose on Day 5. Plasma harvested from each blood sample was divided into two parts: approximately 5 mL for bioassay and the remainder of the sample for high performance liquid chromatographic (HPLC) assay. Plasma samples were assayed for clarithromycin at BAS Analytics (West Lafayette, Ind.) using a validated high performance liquid chromatographic procedure.

Pharmacokinetic Analyses

Pharmacokinetic parameter estimates were calculated using noncompartmental methods. For the Day 1 data, the parameters estimated included $C_{max}$, $T_{max}$, $AUC_{0-\infty}$ or $AUC_{0-48}$, and $t_{1/2}$. For the Day 5 data, the parameters estimated included $C_{max}$, $T_{max}$, $C_{min}$, $AUC_{0-24}$, and DFL.

Statistical Analyses

No statistical analyses were performed on the bioassay data. Analyses of variance (ANOVA) were performed for Day 1 and Day 5 pharmacokinetic variables with effects for regimen, period, sequence, and subject nested within sequence. The $C_{max}$ and $AUC_{0-\infty}$ values for Regimen C were normalized to a 1000 mg dose. For the Day 1 and Day 5 AUC and $C_{max}$ values and for the Day 5 DFL values for both analytes, logarithmic transformation was employed. Each of the Regimens A and B were compared to the reference Regimen C at a significance level of 0.05. Within the framework of the ANOVAs for the Day 5 AUC values, equivalence of the ER formulations of the invention to the IR reference tablet was assessed using the two one-sided tests procedure via 90% confidence intervals.

Figure 2:
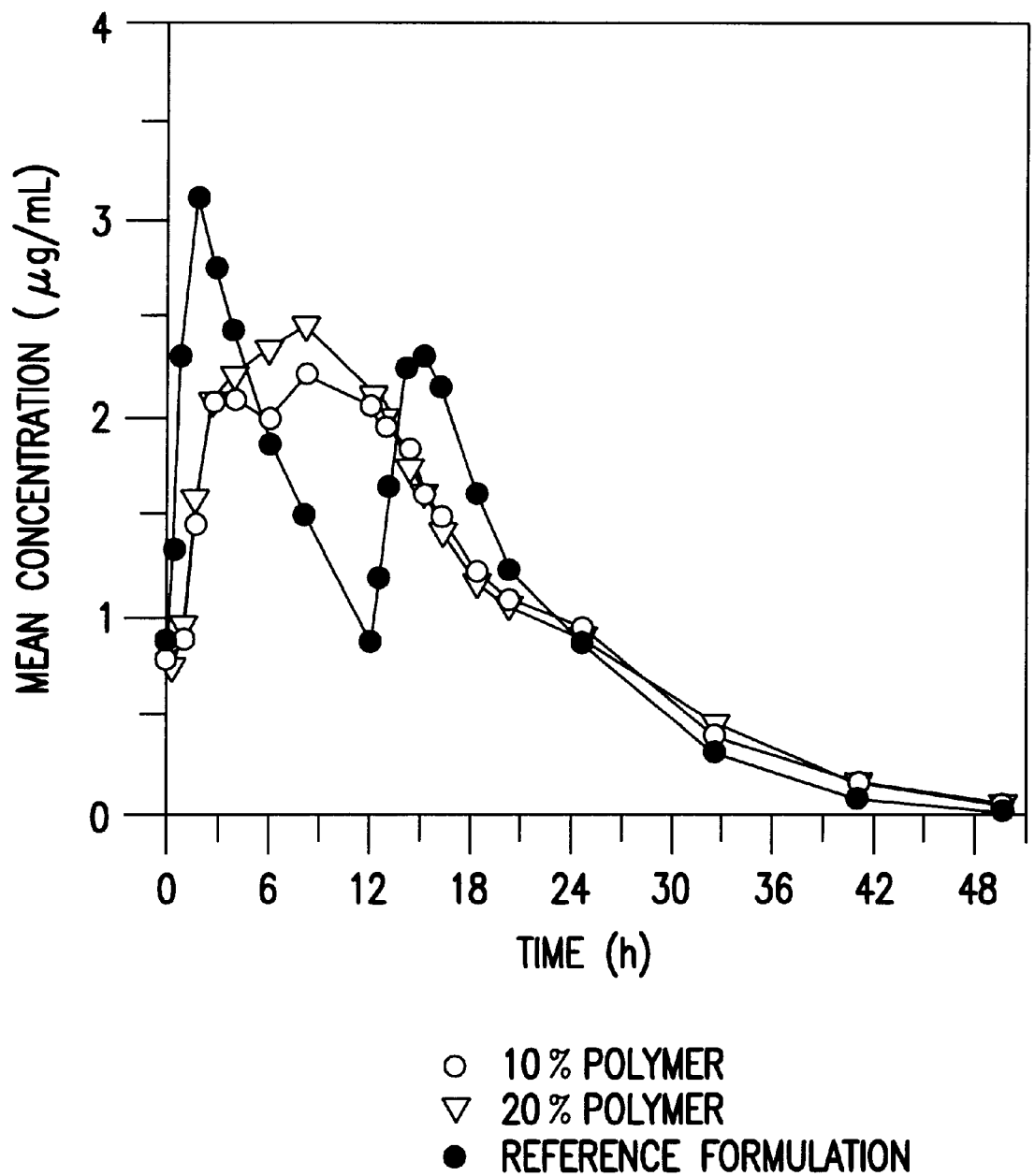
FIG. 2 illustrates the mean in vivo plasma concentration-time profiles following multiple doses of each of the two ER tablets containing 10% or 20%, respectively, of hydroxypropylmethyl cellulose K100 LV as compared to the reference IR tablet. The dosage forms included two 500 mg ER tablets given once daily or one IR 500 mg clarithromycin every 12 hours, respectively, administered for three days with food.
Figure 3:
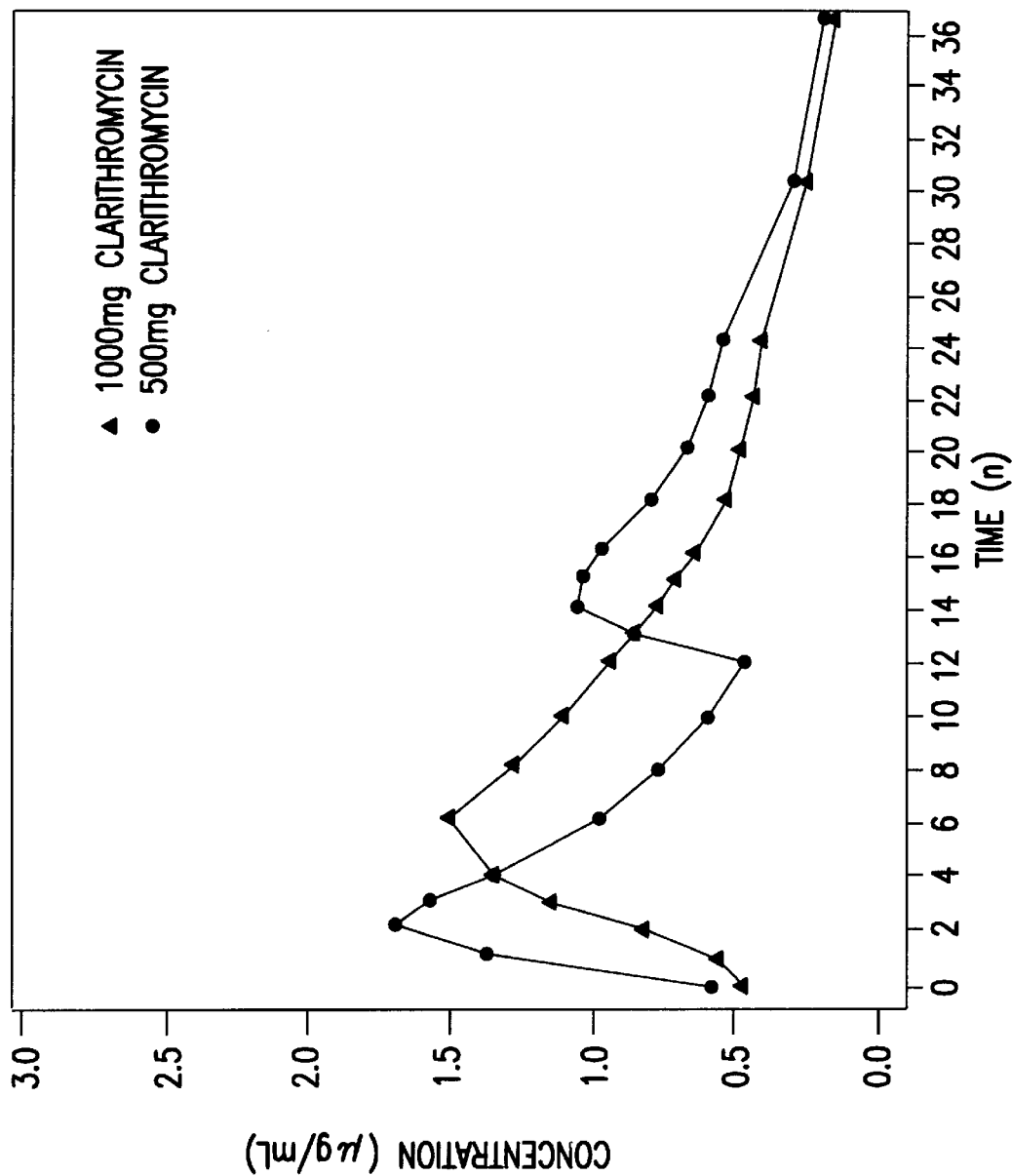
FIG. 3 illustrates the mean in vivo plasma concentration-time profiles following multiple doses of clarithromycin once-daily 1000 mg (not an example of the invention) and IR 500 mg twice-a-day.

The mean plasma concentration-time profiles for the multiple-dose study are illustrated in FIG. 2.

Table IV summarizes (mean±SD) of the Day 5 pharmacokinetic parameter estimates for the clarithromycin in the ER and IR formulations.

TABLE IV

| Formulation | $C_{max}$ (µg/ml) | $C_{max}$ (µg/ml) | $T_{max}$ (h) | $AUC_{0-24}$ (µg·h/mLO) | Fluctuation Index |
|---|---|---|---|---|---|
| A | 2.45 ± 0.69* | 0.70 ± 0.37 | 8.6 ± 4.4* | 39.6 ± 12.8 | 1.11 ± 0.31*† |
| B | 2.66 ± 0.87* | 0.67 ± 0.39 | 6.9 ± 3.3* | 40.2 ± 13.8 | 1.24 ± 0.37* |
| IR Reference | 3.21 ± 0.78 | 0.78 ± 0.29 | 1.9 ± 0.6 | 40.8 ± 11.8 | 1.47 ± 0.26 |

*Statistically significantly different from the reference IR formulation.
†Statistically significantly different from Regimen B.

Point estimates of the relative bioavailability and 90% confidence intervals for the two one-sided tests procedures of Day 5 $AUC_{0-24}$ are set forth in Table V below. The results presented are for logarithmic-transformed clarithromycin $AUC_{0-24}$ values.

TABLE V

| Formulation Comparison | Relative Bioavailability | |
|---|---|---|
| | Point Estimate | 90% Confidence Interval |
| A vs Reference | 0.964 | 0.893–1.039 |
| B vs Reference | 0.970 | 0.899–1.046 |

For this multiple dose study under nonfasting conditions, both the 10% and 20% polymer ER formulations were bioequivalent to the reference IR tablet with respect to the $AUC_{0-24}$. The significantly lower $C_{max}$ central values and later $T_{max}$ values suggest that both the formulations provide extended release of clarithromycin in vivo. The significantly lower DFLs indicate that plasma concentrations fluctuate less for the ER tablet regimens than for the IR tablet regimen. Additionally, the significantly lower DFL for Regimen A compared to Regimen B indicates that plasma concentrations from the 20% polymer fluctuate less than those from the 10% polymer tablet.

Adverse Effects

The adverse effects, including taste perversion (taste profile), were studied for the multiple-dose regimes described above.

Multiple-Dose Study

The formulations A and B of Example 1 (500 mg tablets) and the IR BIAXIN (reference) 500 mg tablet were administered to healthy subjects in a multiple-dose regimen as described above.

Formulations of the Invention

A single dose (2×500 mg) of the formulations A and B of Example 1, was administered to the subjects, followed by a 48 hour wash-out period. Multiple dosing in the morning with the 2×500 mg regimen, once-a-day, followed the wash-out for the next three days.

REFERENCE

A single dose of 500 mg IR BIAXIN tablet was administered to the subjects, followed by a 48 hour wash-out period. Multiple dosing with the 500 mg tablet, twice-a-day followed the washout for three days.

The adverse effects to the body as a whole, cardiovascular system, digestive system, nervous system, respiratory system, skin and appendages, and special senses were measured by monitoring the subjects at regular time intervals. Subjects who reported the same COSTART term more than once were counted only once for that COSTART term.

The results of the adverse effects are set forth in Table VI below.

TABLE VI

| | DOSING REGIMEN | | |
|---|---|---|---|
| | Percent of Total Subjects | | |
| BODY SYSTEM COSTART TERM | A ($N_m$ 24) | B ($N_m$ 23) | Reference ($N_m$ 23) |
| Overall | 9 (37.5%) | 10 (43.5%) | 11 (47.8%) |
| Body As A Whole | 6 (25.0%) | 3 (13.0%) | 1 (4.3%) |
| Asthenia | 2 (8.3%) | 1 (4.3%) | 0 (0.0%) |
| Chills | 0 (0.0%) | 1 (4.3%) | 0 (0.0%) |
| Headache | 2 (8.3%) | 2 (8.7%) | 0 (0.0%) |
| Neck Rigidity | 1 (4.2%) | 0 (0.0%) | 0 (0.0%) |
| Pain | 2 (8.3%) | 0 (0.0%) | 1 (4.3%) |
| Cardiovascular System | 1 (4.2%) | 0 (0.0%) | 0 (0.0%) |

TABLE VI-continued

| | DOSING REGIMEN | | |
|---|---|---|---|
| | Percent of Total Subjects | | |
| BODY SYSTEM COSTART TERM | A ($N_m$ 24) | B ($N_m$ 23) | Reference ($N_m$ 23) |
| Hypertension | 1 (4.2%) | 0 (0.0%) | 0 (0.0%) |
| Digestive System | 4 (16.7%) | 4 (17.4%) | 4 (17.4%) |
| Abdominal Pain | 1 (4.2%) | 0 (0.0%) | 0 (0.0%) |
| Constipation | 0 (0.0%) | 0 (0.0%) | 2 (8.7%) |
| Diarrhea | 2 (8.3%) | 3 (13.0%) | 1 (4.3%) |
| Dyspepsia | 2 (8.3%) | 2 (8.7%) | 1 (4.3%) |
| Flatulence | 0 (0.0%) | 1 (4.3%) | 0 (0.0%) |
| Nausea | 0 (0.0%) | 0 (0.0%) | 1 (4.3%) |
| Nervous System | 0 (0.0%) | 1 (4.3%) | 2 (8.7%) |
| Depersonalization | 0 (0.0%) | 1 (4.3%) | 0 (0.0%) |
| Hypesthesia | 0 (0.0%) | 1 (4.3%) | 1 (4.3%) |
| Insomnia | 0 (0.0%) | 1 (4.3%) | 0 (0.0%) |
| Somnolence | 0 (0.0%) | 0 (0.0%) | 1 (4.3%) |
| Respiratory System | 1 (4.2%) | 1 (4.3%) | 3 (13.0%) |
| Cough Increased | 1 (4.2%) | 0 (0.0%) | 0 (0.0%) |
| Hiccup | 0 (0.0%) | 0 (0.0%) | 1 (4.3%) |
| Pharyngitis | 0 (0.0%) | 1 (4.3%) | 2 (8.7%) |
| Rhinitis | 1 (4.2%) | 1 (4.3%) | 0 (0.0%) |
| Skin and Appendages | 0 (0.0%) | 2 (8.7%) | 2 (8.7%) |
| Rash | 0 (0.0%) | 1 (4.3%) | 1 (4.3%) |
| Skin Disorder | 0 (0.0%) | 1 (4.3%) | 2 (8.7%) |
| Special Senses | 3 (12.5%) | 3 (13.0%) | 6 (26.1%) |
| Eye Disorder | 0 (0.0%) | 1 (4.3%) | 0 (0.0%) |
| Taste Perversion | 3 (12.5%) | 2 (8.7%) | 6 (26.1%) |

It is evident from the above Table VI that the adverse effects to the digestive, nervous and respiratory systems normally associated with BIAXIN are reduced with the ER tablets. The taste perversion with the formulations of the invention is significantly reduced. It is reasonably believed that the reduced adverse effects, particularly taste perversion, would lead to better compliance and a higher incidence of completion of the prescribed treatment regimen.

Comparative Example 3

The results of a comparative pharmacokinetic study of the controlled release formulation A of the co-owned, pending U.S. patent application Ser. No. 08/574,877, filed Dec. 19, 1995, as compared with the IR (BIAXIN) are set forth in Table VII below.

TABLE VII

| PK-Parameter | Unit | Clarithromycin 1000 mg Once-Daily (Formulation A) | | Clarithromycin 500 mg BID Reference (BIAXIN) | | Point Estimator[c] | 90% Confidence Interval |
|---|---|---|---|---|---|---|---|
| | | Mean[a] | S.D.[b] | Mean[a] | S.D.[b] | | |
| $AUC_{0-24}$ | (μg*h/ml) | 27.298 | 10.086 | 28.256 | 10.770 | 97.4 | 86.9–109.2 |
| $C_{max}$ | (μg/ml) | 2.432 | 0.905 | 2.701 | 0.785 | 89.0 | 78.2–101.3 |
| $T_{max}$ | (h) | 5.217 | 1.858 | 2.043 | 0.706 | | |
| $C_{min}$ | (μg/ml) | 0.469 | 0.292 | 0.597 | 0.241 | 71.7 | 60.0–85.7 |
| DFL | | 1.800 | 0.572 | 1.900 | 0.616 | | |

[a]arithmetic means
[b]standard deviation
[c]defined as the ratio of the geometric means of test vs. reference formulation The mean DFL values for the controlled release formulation and for the IR are substantially equal in value as can be seen in the above Table. cf. 1.800±0.572 (for controlled release) with 1.900±0.616 (IR).

The mean DFL for the composition of the invention is statistically lower than the IR in vivo profile. The lower DFL indicates that the ER formulations of the invention provide less variable clarithromycin concentrations throughout the day than the IR and the sustained release compositions.

We claim:

1. A pharmaceutical composition for extended release of an erythromycin derivative in the gastrointestinal environment, comprising an erythromycin derivative and from about 5 to about 50% by weight of a pharmaceutically acceptable polymer, so that when ingested orally, the composition induces statistically significantly lower mean fluctuation index in the plasma than an immediate release composition of the erythromycin derivative while maintaining bioavailability substantially equivalent to that of the immediate release composition of the erythromycin derivative.

2. The pharmaceutical composition of claim 1, wherein the polymer is a hydrophilic water-soluble polymer.

3. The pharmaceutical composition of claim 2, wherein the polymer is selected from the group consisting of polyvinylpyrrolidine, hydroxypropyl cellulose, hydroxypropylmethyl cellulose, methyl cellulose, vinyl acetate/crotonic acid copolymers, methacrylic acid copolymers, maleic anhydride/methyl vinyl ether copolymers and derivatives and mixtures thereof.

4. A pharmaceutical composition for extended release of an erythromycin derivative in the gastrointestinal environment, comprising an erythromycin derivative and from about 5 to about 50% by weight of a pharmaceutically acceptable polymer, so that upon oral ingestion, maximum peak concentrations of the erythromycin derivative are lower than those produced by an immediate release pharmaceutical composition, and area under the concentration-time curve and the minimum plasma concentration are substantially equivalent to that of the immediate release pharmaceutical composition.

5. A method of using an extended release, pharmaceutical composition comprising an erythromycin derivative and from about 5 to about 50% by weight of a pharmaceutically acceptable polymer, comprising administering the composition in an effective amount for the treatment of bacterial infection in a mammal, whereby an area under the concentration-time curve substantially equivalent to that for an immediate release pharmaceutical composition of the erythromycin derivative is maintained.

6. An extended release pharmaceutical composition comprising an erythromycin derivative and a pharmaceutically acceptable polymer, the composition having an improved taste profile as compared to the immediate release formulation.

7. The extended release pharmaceutical composition according to claim 3, wherein the polymer is hydroxypropylmethyl cellulose.

8. The extended release pharmaceutical composition according to claim 7, wherein the hydroxypropylmethyl cellulose is a low viscosity cellulose with viscosity ranging from about 50 to about 200 cps.

9. The extended release pharmaceutical composition according to claim 8, wherein the viscosity of the polymer is about 100 cps.

10. The extended release pharmaceutical composition according to claim 2, wherein the composition comprises from about 5 to about 45% by weight of the polymer.

11. The extended release pharmaceutical composition according to claim 2, wherein the composition comprises from about 45 to about 60% by weight of the erythromycin derivative.

12. The extended release pharmaceutical composition according to claim 11, wherein the composition comprises about 50% by weight of the erythromycin derivative.

13. The extended release pharmaceutical composition according to claim 10, wherein the composition comprises from about 10 to about 30% by weight of the polymer.

14. The extended release pharmaceutical composition according to claim 13, wherein the composition comprises from about 10 to about 30% by weight of hydroxypropylmethyl cellulose having a viscosity of about 100 cps.

15. The extended release pharmaceutical composition according to claim 14, wherein the erythromycin derivative is clarithromycin.

16. The extended release pharmaceutical composition according to claim 15, wherein the composition comprises about 50% by weight of clarithromycin.

* * * * *